United States Patent
Bjerregaard et al.

(10) Patent No.: US 8,574,206 B2
(45) Date of Patent: Nov. 5, 2013

(54) INTESTINAL IRRIGATION DEVICE AND METHOD OF USING THE DEVICE

(75) Inventors: Henrik Bork Bjerregaard, Brønshøj (DK); Niels Balle, Copenhagen Ø (DK); Christian Dorfelt, Virum (DK)

(73) Assignee: MBH-International A/S, Allerød (DK)

( * ) Notice: Subject to any disclaimer, the term of this patent is extended or adjusted under 35 U.S.C. 154(b) by 534 days.

(21) Appl. No.: 12/738,290

(22) PCT Filed: Oct. 30, 2007

(86) PCT No.: PCT/IB2007/054401
§ 371 (c)(1),
(2), (4) Date: Apr. 15, 2010

(87) PCT Pub. No.: WO2009/056906
PCT Pub. Date: May 7, 2009

(65) Prior Publication Data
US 2010/0234821 A1 Sep. 16, 2010

(51) Int. Cl.
*A61F 5/44* (2006.01)
(52) U.S. Cl.
USPC .......................................................... 604/328
(58) Field of Classification Search
USPC .......................................................... 604/328
See application file for complete search history.

(56) References Cited

U.S. PATENT DOCUMENTS

| | | | | |
|---|---|---|---|---|
| 3,292,625 A | * | 12/1966 | Marsan | 604/334 |
| 3,385,298 A | * | 5/1968 | Fenton | 604/332 |
| 3,618,606 A | * | 11/1971 | Brown et al. | 604/334 |
| 3,672,370 A | | 6/1972 | Marsan | 128/227 |
| 3,802,418 A | * | 4/1974 | Clayton | 600/562 |
| 3,910,274 A | * | 10/1975 | Nolan | 604/277 |
| 3,916,897 A | * | 11/1975 | Elmore et al. | 604/179 |
| 4,004,589 A | * | 1/1977 | Neumeier | 604/278 |
| 4,030,500 A | * | 6/1977 | Ronnquist | 604/328 |
| 4,050,461 A | * | 9/1977 | Ruby | 604/277 |
| 4,067,335 A | * | 1/1978 | Silvanov | 604/328 |
| 4,117,847 A | * | 10/1978 | Clayton | 604/97.01 |
| 4,182,332 A | | 1/1980 | Delaney | 128/283 |
| 4,586,927 A | | 5/1986 | Jensen | 604/342 |
| 4,596,554 A | * | 6/1986 | Dastgeer | 604/540 |

(Continued)

FOREIGN PATENT DOCUMENTS

EP 0 150 277 8/1995

OTHER PUBLICATIONS

Notification of Transmittal of theInternational Search Reportand the Written Opinion of the International Searching Authority, or the Declaration, PCT/IB2007/054401, mailed Jul. 2, 2008.

*Primary Examiner* — Leslie Deak
*Assistant Examiner* — Guy K Townsend
(74) *Attorney, Agent, or Firm* — Winston & Strawn LLP

(57) ABSTRACT

An intestinal irrigation device that includes a waste collection bag and a rectal catheter. The rectal catheter has a first end for coupling with the waste collection bag and a free end for insertion into the rectum, while the waste collection bag has a first wall circumferentially united with an opposing second wall and an inlet opening for irrigated waste. The inlet opening has a first coupling part for coupling the rectal catheter into fluid communication with the bag, and the bag has a second coupling part inside it for mating the first coupling part. The device provides a time saving alternative to known devices, and no odor emissions and unpleasant smell is recognized during the irrigation procedure.

14 Claims, 5 Drawing Sheets

(56) References Cited

U.S. PATENT DOCUMENTS

Figure 7:
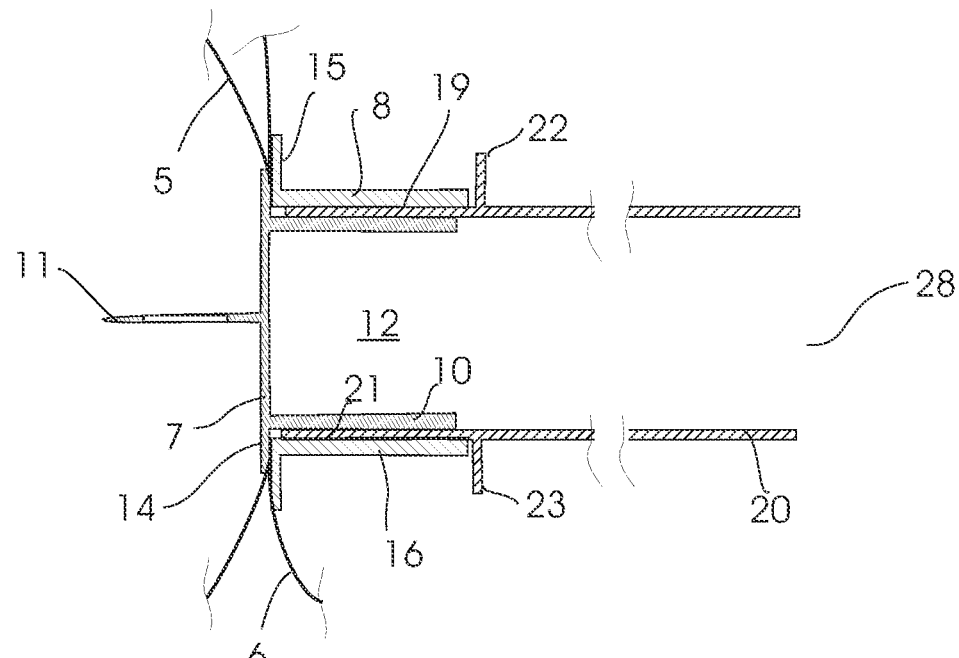

| Patent | | Date | Inventor | Class |
|---|---|---|---|---|
| 4,721,508 A | * | 1/1988 | Burton | 604/338 |
| 4,772,260 A | * | 9/1988 | Heyden | 604/45 |
| 4,986,822 A | * | 1/1991 | Anderson | 604/276 |
| 5,261,898 A | * | 11/1993 | Polin et al. | 604/328 |
| 5,470,325 A | * | 11/1995 | Fundock | 604/332 |
| 5,624,419 A | | 4/1997 | Ersek et al. | 604/355 |
| 5,735,301 A | * | 4/1998 | Rower | 134/167 R |
| 5,738,661 A | * | 4/1998 | Larice | 604/180 |
| 6,033,390 A | * | 3/2000 | von Dyck | 604/332 |
| 6,485,476 B1 | * | 11/2002 | von Dyck et al. | 604/332 |
| 6,569,132 B1 | * | 5/2003 | Dvarsater | 604/328 |
| 7,147,627 B2 | * | 12/2006 | Kim et al. | 604/327 |
| 2003/0229324 A1 | * | 12/2003 | King | 604/339 |
| 2004/0039348 A1 | * | 2/2004 | Kim et al. | 604/264 |
| 2005/0027266 A1 | | 2/2005 | Howlett | 604/317 |
| 2006/0189951 A1 | * | 8/2006 | Kim et al. | 604/327 |
| 2006/0189957 A1 | | 8/2006 | Howlett | 604/403 |
| 2007/0049878 A1 | * | 3/2007 | Kim et al. | 604/327 |

* cited by examiner

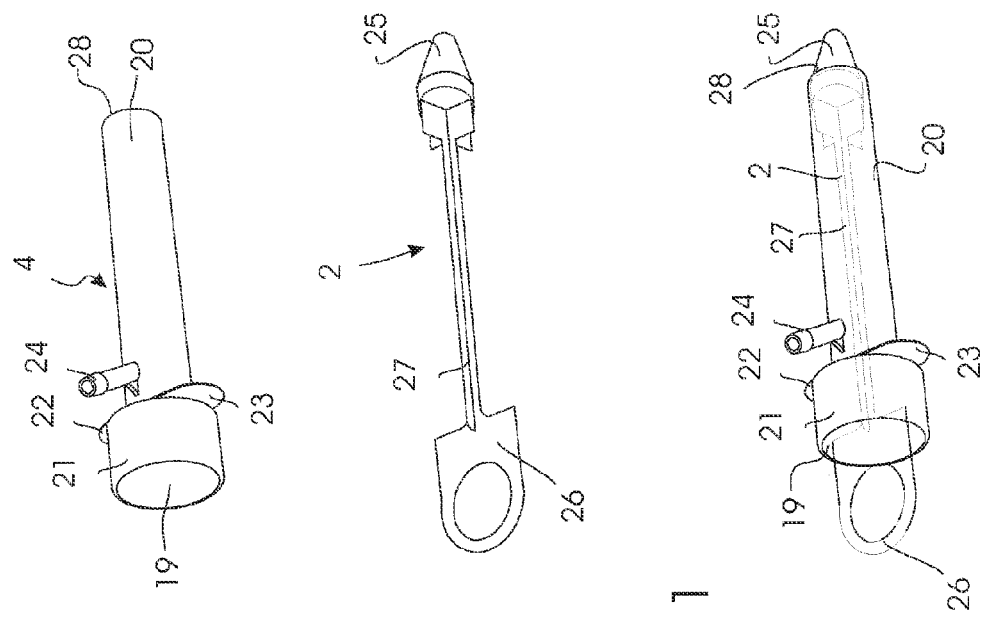
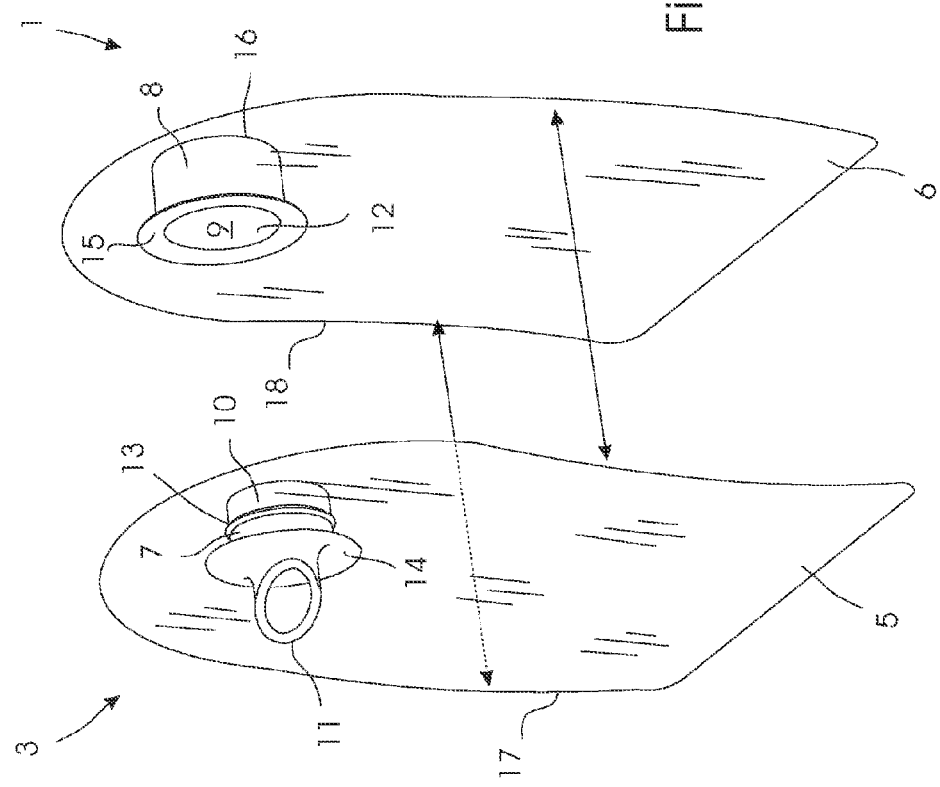

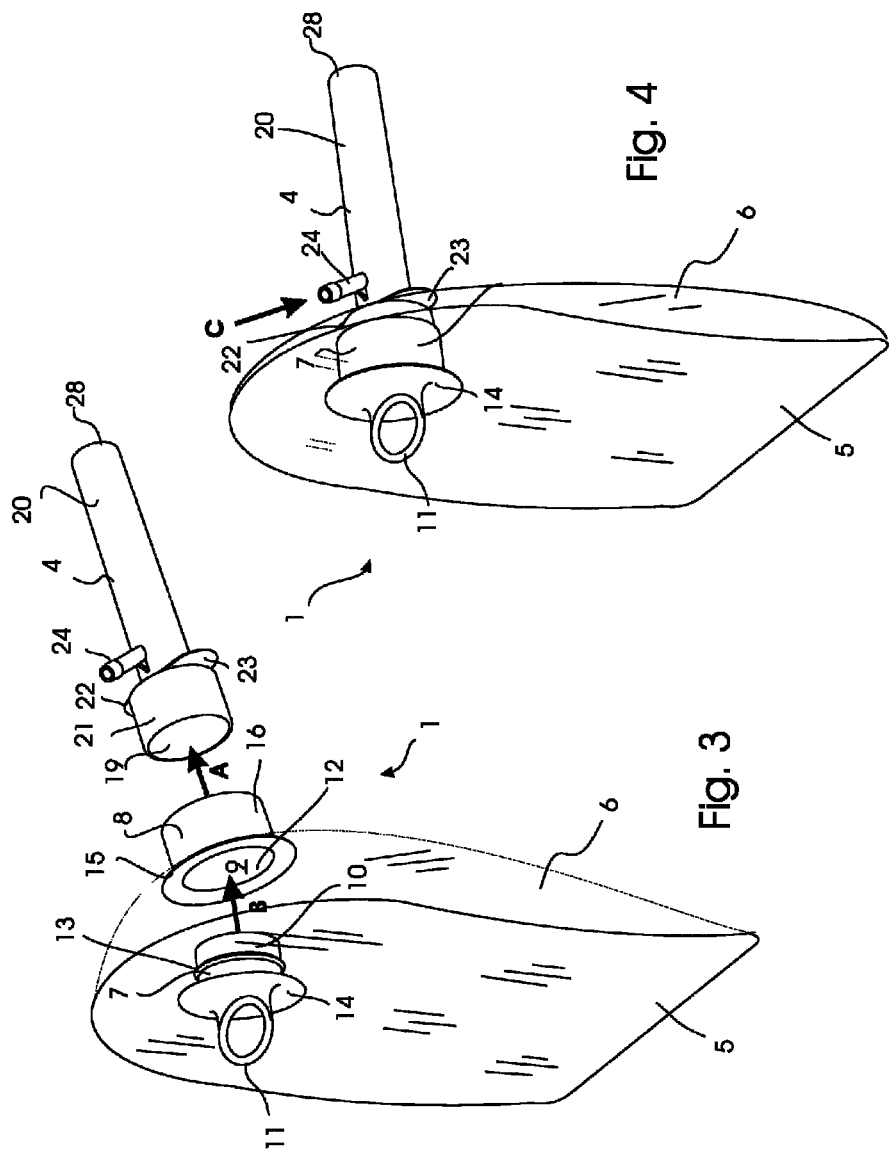

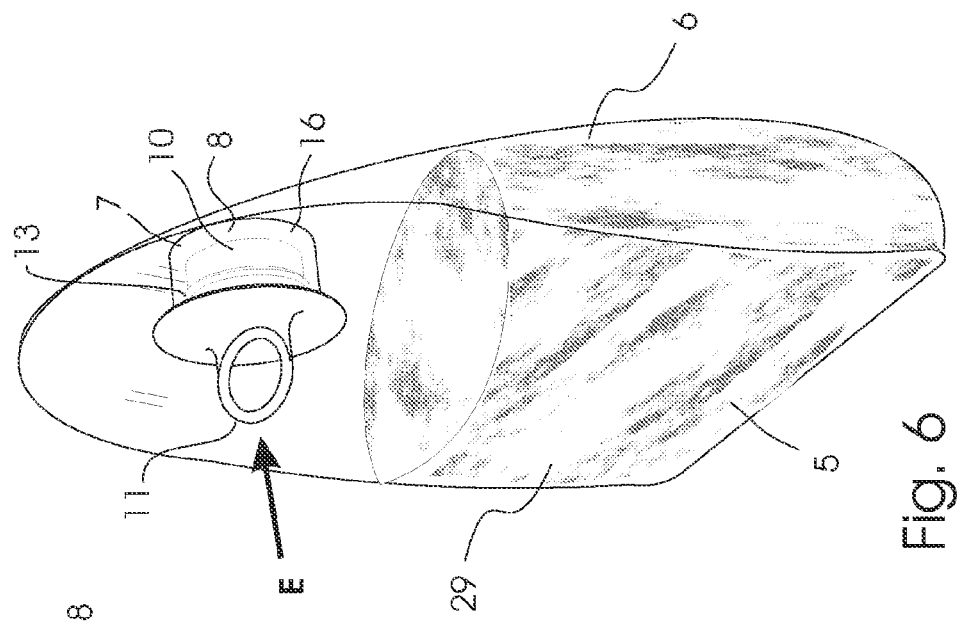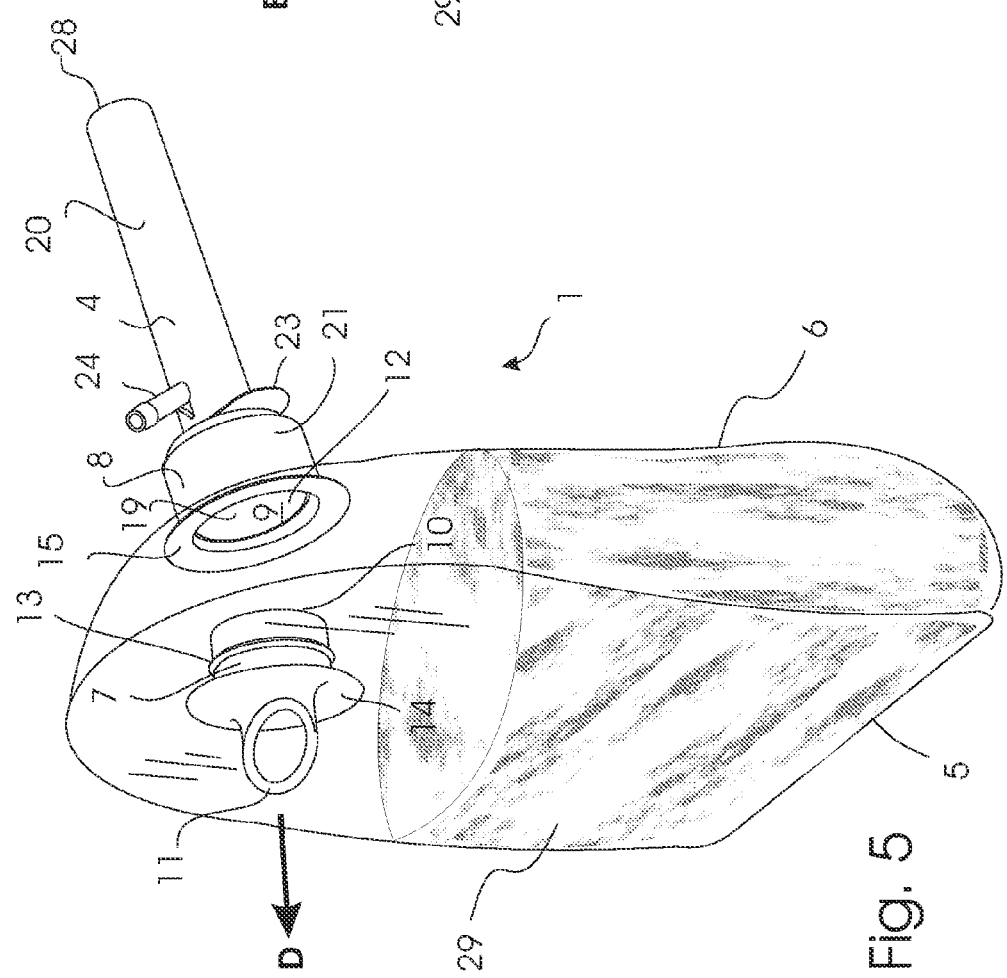

INTESTINAL IRRIGATION DEVICE AND METHOD OF USING THE DEVICE

This application is a 371 filing of International Patent Application PCT/IB2007/054401 filed Oct. 30, 2007.

BACKGROUND

The present invention relates to an intestinal irrigation device comprising a waste collection bag and a rectal catheter, the rectal catheter has a first end for coupling with the waste collection bag and a free end for insertion into the rectum, the waste collection bag has a first wall circumferentially united with an opposing second wall and an inlet opening for irrigated waste.

The rectum is a temporary storage for faeces. As the rectal walls expand due to the materials filling it from within the desire to defecate increases. Peristaltic movements forces the faeces out of the rectum and the sphincter allows the faeces to pass out. If defecation for some reason is not attended to the faeces stays in the colon where more water is absorbed resulting in that the faeces hardens. This condition can be extremely painful, and can in severe cases involve fecal impaction, bowel obstruction and obstipation. Also paradoxical diarrhea where soft stool from the small intestine bypasses the impacted stool is seen as a major problem for many people.

A number of people are not able to move onto a toilet to defecate. The reasons for this may e.g. be traumas, deceases, age, or they may be newly operated. For example spinal cord injury patients require assistance when defecating. For these groups of bedridden people defecation is preformed laying in bed either as an unplanned event or helped by caring staff using various means for facilitating evacuation. These means can be a combination of stimulation, laxatives, suppositories, or other medical interventions or pure mechanical evacuation.

In summary many people have problems defecating e.g. due to their digestive system being constipated, because they are bedridden, or combinations of these conditions.

Enemas has been used since ancient times for aiding people evacuating their intestines. An irrigation liquid is administered to the intestines, preferably both the rectum and colon, via the anus. The irrigation liquid softens the hard faeces so it is able to evacuate suspended in the administered irrigation liquid.

In any of the above referred situations including having difficulties in defecation and suffering from involuntary defecation, e.g. encopresis, people may benefit from aided defecation.

A conventional transanal irrigation device consists of a silicone catheter provided with an inflatable balloon. The catheter is introduced in the rectum and the baloon is inflated to keep the catheter fixed inside the rectum, and further to prevent leakage via the anal canal during the subsequent irrigation. The faecal matter subsequently evacuated from the patient is collected in a bedpan or spills into the bed sheets or absorbent matter, such as towels, single use absorbent sheets, etc. This procedure is time consuming, not dignifying for neither the caring person nor the patient, it soils the environment both with irrigated matter and unpleasant smell and the patient needs washing afterwards.

New more hygienic and dignifying solutions for performing various degrees of intestinal irrigation are in great demand.

SUMMARY OF THE INVENTION

It is a main aspect according to the present invention to provide a novel intestinal irrigation device of the kind mentioned in the opening paragraph that makes it possible to perform intestinal irrigation without the patient and the surroundings getting soiled.

In a second aspect according to the present invention is provided an intestinal irrigation device of the kind mentioned in the opening paragraph that is closeable and easy to dispose after use.

In a third aspect according to the present invention is provided an intestinal irrigation device of the kind mentioned in the opening paragraph that is inexpensive to manufacture and is simple and reliable to use.

The novel and unique whereby this is achieved is the fact that the inlet opening has a first coupling part for coupling the rectal catheter into fluid communication with the waste collection bag, and the waste collection bag has a second coupling part inside the waste collection bag for mating the first coupling part.

In the first step of an irrigation procedure the irrigation liquid is infused to the intestinal organs which need aided evacuation. The irrigation liquid softens hard matter inside at least the rectum and the lower colon and the irrigation liquid including suspended and/or softened matter can expediently be evacuated and collected into the waste collection bag through the inlet opening in the waste collection bag. The first coupling part, which is arranged at the inlet opening, serves both as a reliable securing means for the rectal catheter and for receiving the second coupling part during infusing the irrigation liquid and after completion of the evacuation and termination of the irrigation. The second coupling part is inserted into the first coupling part both when the irrigation liquid is infused to the intestine and again after completion of evacuation of the infused irrigation liquid. No unpleasant smells and soiling accompany this novel very discrete irrigation procedure.

In an embodiment which is especially simple to manufacture and use, the inlet opening may be provided in the second wall, i.e. the wall facing towards the patient during the irrigation procedure, and the second coupling part may protrude inside the waste collection bag from the first wall, i.e. the wall farthest from the patient and accessible during the irrigation procedure, substantially opposite the inlet opening. When the second coupling part faces the first coupling part the mating of these parts are particular easy to perform, in particular after termination of the irrigation where the waste collection bag is full of irrigated matter.

Preferably the first coupling part is a hollow tubular first coupling part having a part designed to receive the rectal catheter, which part fits into or surrounds an annular part of a second coupling part which is operable from outside the waste collection bag to mate and/or engage with the female tubular first coupling part.

Within the scope of the present invention the hollow first coupling part and the second coupling part may be given any appropriate complementary designs, which provide for mating of the parts to obtain closure and/or sealing of the empty waste collection bag during infusion of irrigation liquid and of the full waste collection bag after the rectal catheter has been removed from its position inside the rectum following irrigation. The first coupling part can for example be made as a female cylindrical connecting piece or connecting pipe extending through the wall of the waste collection bag or protruding from the exterior wall, and the second coupling part may be complementary shaped as a solid or hollow male blind plug. Alternatively, the first coupling part and the second coupling part may be designed with snap fitting means such as annular key and slot, or vice versa, or the second coupling part may fit around the exterior diameter of a part of the first coupling part protruding a short distance inside the waste collection bag. The rectal catheter, a coupling end of which may be annularly inserted between the overlapping parts of the first coupling part and the second coupling part, may provide annular sealing depending on dimensioning of the diameters of the coupling parts and the catheter.

If the rectal catheter is detachable attached to the first coupling part the rectal catheter can be inserted as a separate part which also is easy to detach when the closed waste collection bag are to be disposed. If desired or required for sealing the rectal catheter can remain on the closed waste collection bag to be jointly disposed off.

In an advantageously embodiment according to the present invention the rectal catheter is configured as a dimensionally stable, tubular structure which has an inlet opening for infusing the irrigation liquid. The dimensionally stable structure advantageously keeps the rectum distended during the period the rectal catheter is inserted. The sphincter clamps in a tight fitting manner around the exterior face of the non-collapsible rectal catheter and provides a sealing capacity that for a normal functioning sphincter is sufficient to prevent leakage. Due to the dimensional stability of the rectal catheter the rectal catheter does not collapse in response to peristaltic movements and/or intestinal force and a free flow pathway is sustained both during infusion of irrigation liquid and during the subsequent evacuation of waste. No balloon is required for keeping the intestines distended and in place as in conventional devices for performing irrigations. The internal diameter of the intestinal canal around the rectal catheter is kept open and substantially constant by the dimensionally stable structure of the rectal catheter itself. Moreover, the dimensionally stable structure does not curl up or kink during insertion into the rectum as is the risk when using conventional flexible rubber or plastic catheters.

In order to preform a gentle, less painful and anatomical more acceptable insertion the rectal catheter may be given a tapered free end opposite the end which is designed for engaging the first and/or second coupling part of the waste collection bag.

The diameter of the rectal catheter may vary in dependency of anatomical conditions. A child may require a short rectal catheter having a small external diameter contrary to an adult, which is able to accept larger external diameters inside the rectum. Alternatively a catheter having a cone-shaped end may be preferred. The length, external diameter, internal diameter and degree of tapering towards the free end of the rectal catheter are selected in dependency of the required use and the anatomical conditions of the patient. Various standard dimension products and individual combination of rectal catheters and waste collection bags of different sizes are foreseen within the scope of the present invention allowing the patient to select exactly the combination suitable for her/his specific need. Irrespective of choice of waste collection bag or rectal catheter it is preferred that the first coupling part of the waste collection bag and the coupling end of the rectal catheter are made as standard units to allow a plurality of combinations of bags and rectal catheters. Preferably the sealing between the rectal catheter and the first coupling part is leak proofed both in the situation where the second coupling part is engaged with the first coupling part, and in the situation where these coupling parts are disengaged.

The insertion may cause considerable inconvenience to the patient and preferably an introducer may be used for facilitating a gentle insertion. The introducer may e.g. have a pointed blunt tip to aid in alleviating the physical discomfort and pain that the patient may expire during insertion of the rectal catheter.

In a second modified embodiment according to the present invention the introducer has a guide rod, which extends displaceable through the second coupling part with the tip of the introducer located inside the bag. The introducer is in this embodiment not a separate part but can be moved in and out of the catheter so that the tip protrudes from the catheter end and the catheter can be smoothly and gently inserted into the rectum. The tip of the introducer may be dimensioned so that the tip also can serve as a seal inside the catheter. This second embodiment may be very fast to operate and may be preferred for children.

The intestinal irrigation device according to the present invention can be used in a method comprising the steps of inserting the rectal catheter in the rectum, mating the coupling parts to at least substantially close the waste collection bag, mounting the substantially closed waste collection bag on the rectal catheter, infusing the irrigation liquid to at least the rectum intestine, disengaging the first coupling part and the second coupling part, draining the irrigation liquid and irrigated intestinal content into the waste collection bag, removing the rectal catheter from the rectum, engaging the second coupling part and the first coupling part to close the inlet opening of the waste collection bag.

In the above method the rectal catheter may be detached from the closed waste collection bag before disposal in order to meet demands on waste classification for disposal and incineration.

BRIEF DESCRIPTION OF THE INVENTION

Figure 8:
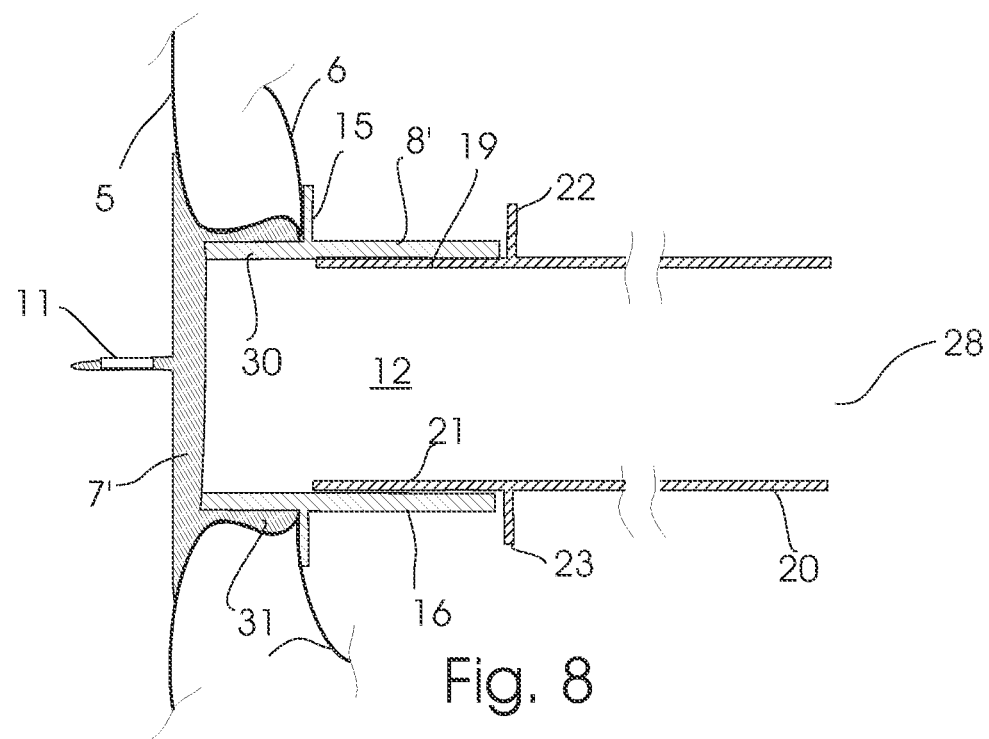
Figure 9:
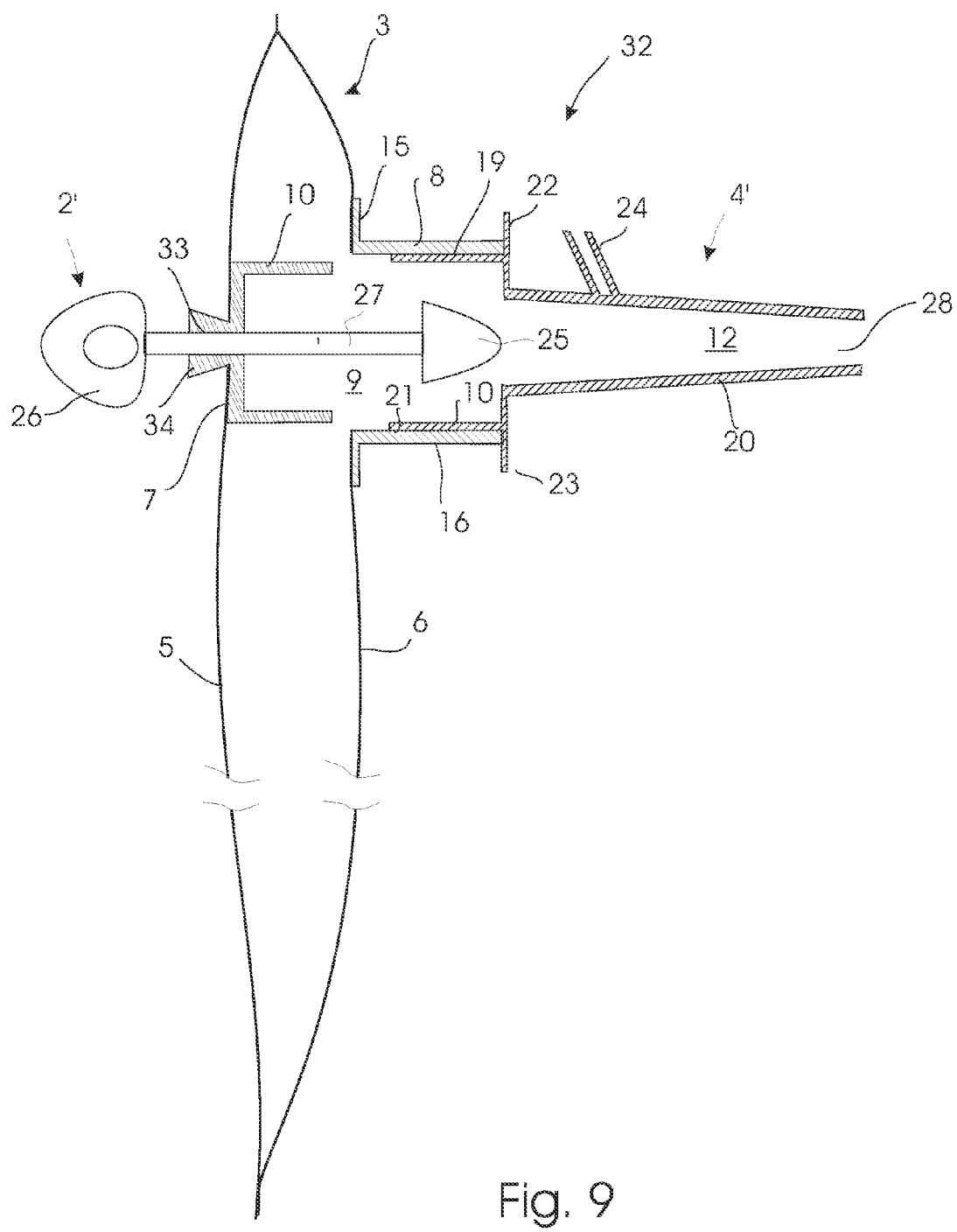

The invention will be explained in greater detail below, describing exemplary embodiments of the intestinal irrigation device with reference to the drawing, in which FIG. 1 shows a perspective exploded view of the components for an exemplary embodiment of an intestinal irrigation device according to the present invention and an introducer for the device, FIG. 2 is a perspective view of the introducer inserted into a detached rectal catheter, FIG. 3 shows a perspective view of the waste collection bag and the rectal catheter for the intestinal irrigation device according to the invention, FIG. 4 shows a perspective view of the waste collection bag and the rectal catheter in assembled state, ready for infusing the irrigation liquid, FIG. 5 shows the waste collection bag during and after evacuation of irrigated matter, where the first coupling part and the second coupling part are disengaged, FIG. 6 shows the intestinal irrigation device after the irrigation has been terminated, the waste collection bag has been closed, and the rectal catheter has been detached, FIG. 7 shows in an enlarged scale an axial, sectional view of a first way of engaging a first coupling, a second coupling part and a rectal catheter, FIG. 8 shows in an enlarged scale an axial, sectional view of a second way of engaging a first coupling part, a second coupling part and a rectal catheter, and FIG. 9 shows a sectional view of a second embodiment intestinal irrigation device according to the present invention.

DETAILED DESCRIPTION OF THE DRAWING

The invention is described below with the assumption that the intestinal irrigation device is used in a transanal irrigation (TAI) procedure. This assumption is not to be construed as limiting, and other more thorough irrigation procedures can also be performed using the device according to the present invention.

In the perspective exploded view of FIG. 1 the components for the intestinal irrigation device 1 is seen together with and introducer 2.

The intestinal irrigation device 1 consist basically of a waste collection bag 3 and a rectal catheter 4.

The waste collection bag 1 is constructed of a first wall 5, facing away from the patient during irrigation, and an opposing second wall 6, facing towards the patient during irrigation. By way of example the walls 5,6 are in the following description indicated as being transparent (seen through) to better illustrate the assembling of the various components belonging to the device 1. Transparency is however optional, but allows monitoring of draining and evacuation, and visual inspection of the evacuated matter.

The first wall 5 has a male second coupling part 7 for engaging a female first coupling part 8 arranged at the inlet opening 9 of the second wall 6.

The second coupling part 7 has a male part 10 protruding inside the waste collection bag 3 towards the female first coupling part 8. The male part 10 extends into a grip 11 outside the waste collection bag 3 so that the second coupling part 7 traverses or is coupled to the first wall 5 in a sealingly manner, enabling the second coupling part 7 to be inserted into and retracted from the bore 12 of the first coupling part 8 from outside the waste collection bag 3. The male part 10 of the second coupling part 7 has in the case shown an annular sealing rim 13. The second coupling part 7 is attached to the first wall 5 by means of an annular attachment part 14 between the male part 10 and the grip 11.

The female first coupling part 8 consists of a securing flange 15 secured to the inlet opening 9 in the second wall 6. The securing flange 15 extends into a tubular connection piece 16 protruding outside the waste collection bag 3 when the first wall 5 and the second wall 6 are united to form the waste collection bag 3. The bore 12 of the tubular connection piece 16 serves for receiving the male part 10 of the second coupling part 7 when the entire device 1 is to be operated. The circumference 17 of the first wall 5 and the circumference 18 of the second wall 6 are united, e.g. using high frequency welding, heat sealing, ultra sonic welding, laser welding or gluing to form the waste collection bag 3. This waste collection bag may e.g. be made of a transparent disposable plastic material such as polyethylene (PE) or ethylene vinyl acetate (EVA), both of which can be incinerated in an inexpensive manner together with usual hospital waste. Also polyvinyl chloride can be used. In case the patient expires the irrigation procedure as particular unaesthetic and prefers to have a very discrete disposal of the waste, the waste collection bag may be coloured or even not transparent, however transparency allows continuously monitoring of the irrigation. Also the waste collection bag 3 may be provided with a means, such a handle (not shown), for facilitating transportation and suspending of the waste collection bag 3.

The rectal catheter 4 consists of a coupling end 19 extending into a tapering cylinder 20 to be inserted into the rectum of a patient through the anus. The rectal catheter 4 is hollow to allow evacuation from the intestine into the waste collection bag 3. At the coupling end 19, the rectal catheter has a circumferential flange part 21 for engaging the bore 12 of the first coupling part 8. The flange part 21 fits sealingly into the bore 12 enabling evacuation of irrigation liquid and intestinal waste material without spillage and leakage. For facilitating handling of the rectal catheter 4 during engaging and disengaging the first coupling part 8 the flange part 21 has opposing protruding flaps or ears 22,23. The tapering cylinder 20 of the rectal catheter 4 has a feeding branch 24 for an infusing irrigation liquid from a reservoir (not shown).

Alternatively the feeding branch can be provided in any of the first and the second coupling parts and a clamp be used for opening and closing supply of irrigation liquid.

The reservoir may be of any suitable kind including open and closed reservoirs, and the irrigation liquid can e.g. be water, saline or any of these including a medical compound promoting dissolution of solid matter in the intestine, promoting peristaltic, or the medical compound may be a drug or medicament beneficial for the intestine, or the patient in general.

The introducer 2 is configured with a pointed but still blunt tip 25, a handle 26 and a guide rod 27 extending between the tip 25 and the handle 26. The blunt tip 25 has a greatest diameter that corresponds the internal diameter of the free, open end 28 of the cylinder 20 of the rectal catheter 3. The tip of the introducer 2 is dimensioned so that the introducer 2 is held in frictional, force-fitting engagement inside the rectal catheter 4 to ensure that the rectal catheter 4 and the introducer 2 remains secured to each other during insertion.

As seen best in FIG. 2 the introducer 2 are inserted into the rectal catheter 4 so that the tip 25 of the introducer 2 protrudes from the open, free end 28 of the catheter 4. The location of the introducer inside the rectal catheter 4 is indicated in dotted line. Both the introducer 2 and the rectal catheter 4 are made of an inexpensive, disposable plastic material. The introducer 2 is optional and the rectal catheter 4 can quite as well be inserted into the rectum without using an introducer 2.

The dimensionally stable rectal catheter 4 housing or not housing the introducer 2 is preferably greased on the exterior face to reduce frictional force during insertion into the rectum.

In use the tip 25 and/or the open free end 28 of the rectal catheter 4 is pointed towards the anus, and the rectal catheter is gently forced inside the rectum. If an introducer 2 is used it is removed and the bore 12 of the tubular connection piece 16 of the first coupling part 8 is mounted around the flange part 21 of the rectal catheter 4, as indicated with the arrow A, to seal the coupling between the rectal catheter and the waste collection bag. Next, as indicated with the arrow B in FIG. 3 the male part 10 of the second coupling part 7 are inserted into the bore 12 of the first coupling part 8 or into the flange part 21 of the rectal catheter 4 from the opposite side to effectively block the access of irrigation liquid to the waste collection bag 3 during infusion. This assembled state is seen best in FIG. 4.

An irrigation source (not shown) is connected to the inlet opening, the feeding branch 24, to establish liquid communication to the intestine, as indicated with the arrow C in FIG. 4. The amount of available infused irrigation liquid may vary but can e.g. be 2000 ml app. 38° C. water of which for example about 500-1000 ml are infused before evacuation is started. Infusion may be facilitated by a pump, pressing on the irrigation liquid container, preferably a plastic waste collection bag, or may simply take place using gravity. How to infuse is of the choice of the operator or the patient. If desired the procedure can be repeated using a portion of the remaining available irrigation liquid, provided the waste collection bag 3 is not full yet or is emptied.

For evacuation the male part 10 of the second coupling part 7 is pulled out of the bore 12 of the first coupling part 8 or of the flange part 21 of the rectal catheter 4, as indicated with the arrows D in FIG. 5 and the infused irrigation liquid and suspended or softened intestinal material 29 is allowed to flow freely from the intestines into the waste collection bag 3 until at least substantially complete evacuation is reached.

The male part 10 of the second coupling part 7 are reinserted into the bore 12 of the female first coupling part 8 to close the full waste collection bag 3, as indicated with the arrow seen in FIG. 6. Optionally the rectal catheter 4 is disengaged and both the rectal catheter 4 and the closed waste collection bag 3 are ready for disposal.

The rectal catheter may or may not be separated from the first coupling part leaving behind the closed waste collection bag, which now appears as an easy disposable unit.

Suitable exterior diameters for standard rectal catheters are between 8-35, and suggested standard diameter are for example about 10-11 mm, 20-21 mm or 30-31. The reservoir for irrigation liquid is preferably suspended at a dropstand or similar means that provide distance between the location of the device and the reservoir that provides for appropriate infusion speed and rate, preferably using gravity. The reservoir may be equipped with a tube for connecting to the rectal catheter 4. Furthermore, the reservoir can be capped to allow for filling it to any desired degree, e.g. with lukewarm tap water.

FIG. 7 shows in an enlarged scale an axial, sectional view of a first way of engaging a first coupling 8, a second coupling part 7 and a rectal catheter 4, as described for the preceding FIGS. 1-6. The circumferential flange part 21 of the coupling end 19 of the rectal catheter 4 is seen inserted into the bore 12 of the first coupling part 8, and the male part 10 is inserted inside the circumferential flange part 21 of the rectal catheter 4. In this embodiment the flange part 21 of the rectal catheter 4 serves as a tight seal between the first coupling part 8 and the second coupling part 7.

In a modified embodiment the exterior diameter of the second coupling part 7's male part 10 and the circumferential flange part 21 of the rectal catheter 4 may be substantially identical, in which case a tight seal is obtained by selecting the internal diameter of the tubular connection piece 16 of the first coupling part 8 to be substantially the same.

FIG. 8 shows in an enlarged scale an axial, sectional view of a second way of engaging a first coupling part 8', a second coupling part 7' and a rectal catheter 4. The embodiment shown in FIG. 8 corresponds substantially to the embodiment shown in FIG. 7 and for like parts like numerals are used.

The first coupling part 8' has a first short tubular extension 30 extending inside the waste collection bag 1 and the second coupling part 7' has a mating second tubular extension 31 fitting tightly and sealingly around the first tubular extension. In this embodiment the rectal catheter can be detached without the waste collections bag 3 subsequently leaks.

If the first and second coupling parts are disengaged from each other the evacuated content in the waste collection can in a simple manner empty into the toilet using the rectal catheter as an outlet canal or spout.

Various outlet means allowing hygienic emptying of the device after evacuation may be provided on e.g. the coupling parts or in the walls of the waste collection bag.

FIG. 9 shows a sectional view of a second embodiment 32 of an intestinal irrigation device according to the present invention. The intestinal irrigation device 32 corresponds substantially to the intestinal irrigation device 1 according to the previously described embodiment and for like parts same reference numerals are used.

The second embodiment of the intestinal irrigation device 32 has a second wall 6 with a first coupling part 8, a first wall 5 with a second coupling part 7, through both of which parts 7,8 a guide rod 27 of a modified introducer 2' extends. The tip 25 of the introducer 2' is retractable positioned inside both the bag 3, the tapered tubular part 20' of the rectal catheter 4' and a through-opening 33 of the second coupling part 7. The tip 25 fits lengthwise movable inside the tubular part 20' so that when the tip 25 is pushed forward against the first coupling part 8 and further inside the tapered tubular part 20' of the catheter 4', the tip 25 can protrude from the free end of the tubular part 20' to facilitate insertion of the catheter 4' into the rectum. Optionally the design of the tip also enhances sealing between catheter 4' and bag 3. Opposite the tip 25 the guide rod 2' of the introducer 2' extends through the through-going opening 33 of the second coupling part 7 into a handle 26 serving for displacing either the introducer 2', the introducer 2' and the second coupling part 7 together, or the introducer 2' and the second coupling part 7 individually, in and out of the rectal catheter and the first coupling part 7,8 for among other things closing the bag during infusion of irrigation liquid via inlet opening 24, and opening of the bag during irrigation when the first 8 and the second coupling part 7 are disengaged.

Hence, in this embodiment 32 the introducer 2' can be moved as a separate part through both the second coupling part 7 and the rectal catheter 4', and the engagement and disengagement of the coupling parts 7,8 are made in a separate action by grasping the externally protruding annular flange 34 of the second coupling part 7 and moving these coupling parts 7,8 towards or against each other, optionally only moving one of the coupling parts 7,8. The through-opening 33 surrounds the guide rod 25 in a fluid tight, optionally frictional manner which also serves the purpose of preventing unintentional moving of the introducer during insertion of the catheter into the rectum.

Modifications and combinations of the above principles and designs are foreseen within the scope of the present invention.

The novel devices provide a time saving alternative to known devices, in that the procedure need not take more than 15-20 minutes and no odour emissions and unpleasant smell is recognized during the irrigation procedure.

What is claimed is:
1. An intestinal irrigation device, comprising:
a waste collection bag having a first wall perimetrically united with an opposing second wall, with the second wall having an inlet opening for directing irrigated waste into the bag; and
a rectal catheter having a first end with a tubular extension for coupling with the inlet opening of the waste collection bag and a free end for insertion into the rectum,
wherein the inlet opening has a first coupling part for coupling the rectal catheter into fluid communication with the waste collection bag, and the waste collection bag has a second coupling part attached to the first wall thereof for mating the first coupling part, wherein the first coupling part comprises a first tubular extension extending inside the waste collection bag, and the second coupling part comprises a grasping member and a mating second tubular extension fitting tightly and sealingly around the first tubular extension, and
wherein mating of the first and second coupling parts is achieved when engaging the first and second tubular extensions with the second tubular extension fitting tightly and sealingly around the first tubular extension to close the bag and prevent fluid communication between the rectal catheter and the waste collection bag either during irrigation or after receiving irrigated waste for disposal, and wherein the first and second coupling parts, when detached, open the waste collection bag and the inlet opening for removal of irrigated waste into the bag through the inlet opening in the second wall thereof; and wherein the grasping member supports the waste collection bag for carrying separate from the rectal catheter and the grasping member can be used to (i) couple the rectal catheter to the waste collection bag; (ii) couple the second tubular extension to the first tubular extension to close the bag and prevent fluid communication between the rectal catheter and the waste collection bag; and (iii) remove the waste collection bag from the rectal catheter while keeping the waste collection bag substantially closed.

2. The intestinal irrigation device according to claim 1, wherein the second coupling part when detached protrudes inside the waste collection bag from the first wall substantially opposite the inlet opening.

3. The intestinal irrigation device according to claim 1, wherein the tubular extension of the first coupling part is a female part designed to receive the hub of the rectal catheter, with the hub fitting tightly and sealingly around the tubular extension of the second coupling part which is operable from outside the waste collection bag to engage with the female tubular first coupling part.

4. The intestinal irrigation device according to claim 1, wherein the rectal catheter is detachably attached to the first coupling part.

5. The intestinal irrigation device according to claim 1, wherein the rectal catheter is a dimensionally stable, tubular structure which has an inlet opening for infusing the irrigation liquid and keeps an internal diameter of the intestinal canal open and substantially constant during insertion into a patient's rectum.

6. The intestinal irrigation device according to claim 1, wherein the rectal catheter has a tapered end.

7. The intestinal irrigation device according to claim 1, which further comprises an introducer for inserting the rectal catheter into the rectum.

8. The intestinal irrigation device according to claim 7, wherein the introducer has a tip and a guide rod which extends displaceably through the second coupling part with the tip of the introducer inside the bag.

9. A method of applying the intestinal irrigation device according to claim 1 to a subject, which method comprises:
inserting the rectal catheter in the rectum;
mating the coupling parts to at least substantially close the waste collection bag;
mounting the substantially closed waste collection bag on the rectal catheter;
infusing the irrigation liquid to at least the rectum intestine,
disengaging the first coupling part and the second coupling part;
draining the irrigation liquid and irrigated intestinal content into the waste collection bag;
removing the rectal catheter from the rectum; and
engaging the second coupling part into the first coupling part to close the inlet opening of the waste collection bag.

10. The method according to claim 9, wherein the rectal catheter is detached from the closed waste collection bag before disposal.

11. The intestinal irrigation device according to claim 1, wherein the perimeter of the first wall and the perimeter of the second wall are united to form the waste collection bag using one of high frequency welding, heat sealing, ultrasonic welding, laser welding or gluing.

12. The method according to claim 9, wherein the tubular extension of the first coupling part is a female part designed to receive the hub of the rectal catheter, with the hub fitting tightly and sealingly around the tubular extension of the second coupling part which is operable from outside the waste collection bag to engage with the female tubular first coupling part.

13. The method according to claim 9, wherein the perimeter of the first wall and the perimeter of the second wall are united to form the waste collection bag using one of high frequency welding, heat sealing, ultrasonic welding, laser welding or gluing.

14. The intestinal irrigation device according to claim 1, wherein the tubular extension of the second coupling part is a male part that includes an annular sealing rim.

\* \* \* \* \*